United States Patent
Fogel et al.

(10) Patent No.: US 8,086,412 B2
(45) Date of Patent: Dec. 27, 2011

(54) CORRECTIVE METHODOLOGY FOR PROCESSING RESULTS OF TRANSCRIPTOME EXPERIMENTS OBTAINED BY DIFFERENTIAL ANALYSIS

(75) Inventors: Paul Fogel, Paris (FR); Didier Zugaj, Nateau sur Essonne (FR); Jean-Marc Le Goff, Marseilles (FR); Jérôme Aubert, Grasse (FR); Sophie Deret, Mougins (FR)

(73) Assignee: Galderma Research & Development, Biot (FR)

( * ) Notice: Subject to any disclaimer, the term of this patent is extended or adjusted under 35 U.S.C. 154(b) by 271 days.

(21) Appl. No.: 12/457,730

(22) Filed: Jun. 19, 2009

(65) Prior Publication Data

US 2010/0057369 A1 Mar. 4, 2010

Related U.S. Application Data

(63) Continuation of application No. PCT/FR2007/052562, filed on Dec. 19, 2007.

(30) Foreign Application Priority Data

Dec. 19, 2006 (FR) .................................... 06 55660

(51) Int. Cl.
G01N 33/48 (2006.01)
G06F 19/00 (2011.01)
(52) U.S. Cl. ................. 702/19; 435/6; 702/20; 702/85; 702/179
(58) Field of Classification Search .................... 702/19, 702/20, 85, 179, 180; 435/6, 7.23
See application file for complete search history.

(56) References Cited

U.S. PATENT DOCUMENTS

| 7,715,990 | B2 * | 5/2010 | Zou et al. ........................ 702/20 |
| 2002/0169562 | A1 * | 11/2002 | Stephanopoulos et al. ..... 702/19 |
| 2007/0231816 | A1 * | 10/2007 | Chaussabel et al. .............. 435/6 |
| 2009/0138209 | A1 * | 5/2009 | Maruhashi et al. ............. 702/20 |
| 2011/0086342 | A1 * | 4/2011 | Esumi et al. ...................... 435/6 |

OTHER PUBLICATIONS

Mansourian et al., "The Global Error Assessment (GEA) model for the selection of differentially expressed genes in microarray data," *Bioinformatics* (Oxford), vol. 20, No. 16, pp. 2726-2737, Nov. 1, 2004, XP002436018.

Yang et al., "Identifying differentially expressed genes from microarray experiments via statistic synthesis," *Bioinformatics* (Oxford), vol. 21, No. 7, pp. 1084-1093, Apr. 2005, XP002436019.

Wang et al., "A generalized likelihood ratio test to identify differentially expressed genes from microarray data," *Bioinformatics* (Oxford), vol. 20, No. 1, pp. 100-104, Jan. 1, 2004, XP002436020.

* cited by examiner

*Primary Examiner* — John H Le

(74) *Attorney, Agent, or Firm* — Buchanan Ingersoll & Rooney, P.C.

(57) ABSTRACT

A corrective method is described for processing results of transcriptome experiments obtained by differential analysis includes the following steps: obtaining the results of the level of expression of genes under a reference condition, and calculating the mean level of expression of each of such genes; obtaining the results of the level of expression of such genes under a treatment condition, and calculating the mean level of expression for each of such genes; calculating the modulation coefficient for the level of expression for each of such genes; calculating a p-value associated with each modulation coefficient; and calculating isobar curves of p-value as a function of the mean level of expression of each of such genes under the reference condition; calculating and associating a median modulation coefficient on the isobar curve of each p-value observed. The processing of results of experiments carried out on DNA chips is also described.

9 Claims, 2 Drawing Sheets

US 8,086,412 B2

CORRECTIVE METHODOLOGY FOR PROCESSING RESULTS OF TRANSCRIPTOME EXPERIMENTS OBTAINED BY DIFFERENTIAL ANALYSIS

CROSS-REFERENCE TO PRIORITY/PCT APPLICATIONS

This application claims priority under 35 U.S.C. §119 of FR 06/55660, filed Dec. 19, 2006, and is a continuation/national phase of PCT/FR 2007/052562, filed Dec. 19, 2007 and designating the United States (published in the French language on Jul. 24, 2008 as WO 2008/087324 A2; the title and abstract were also published in English), each hereby expressly incorporated by reference in its entirety and each assigned to the assignee hereof.

BACKGROUND OF THE INVENTION

1. Technical Field of the Invention

The present invention relates to corrective methods for processing results of transcriptome experiments obtained by differential analysis. It relates more particularly to the processing of such results, in the case of experiments conducted on DNA chips. The object of transcriptome experiments is to identify genes of interest or groups of genes of interest.

2. Description of Background and/or Related and/or Prior Art

Generally, the level of expression of these genes of interest or of these groups of genes of interest vary significantly, for example, in response to a signal. During the analysis of results of transcriptome experiments, for example by means of DNA chips, it is common practice to select the genes exhibiting the greatest modulation, i.e., the greatest variation in their level of expression. The level of this modulation, also called modulation coefficient, is defined as the ratio of the level of expression observed in one experiment, for example under a "treatment" condition, to that observed in another experiment, for example under a "reference" condition.

Examination of the results shows that, the more a high level of modulation is used to restrict the number of genes selected, the more this favors, in the selection made, the emergence of genes of which the level of expression is, under the reference condition, close to the limit of detection. Now, there is no biological argument to explain the reason for which the genes most weakly expressed under the reference condition would be the genes most strongly modulated during a treatment. This selection therefore introduces a bias and results in genes which exhibit a lower level of modulation being ignored simply because they are more highly expressed under the reference condition.

If the expression-level modulation coefficient is estimated on the basis of several observations of the gene on several chips corresponding to the same condition, i.e., on the basis of replicates of the reference condition or of the treatment condition, it is demonstrated that the modulation coefficient and the average level of expression of the genes change conversely [R. Mansourian et al., The global error assessment (GEA) model for the selection of differentially expressed genes in microarray data, Bioinformatics Advance Access, 2004]. In other words, the lower the level of expression of a gene in several replicates of a reference condition, the higher its coefficient of modulation in response to the treatment, calculated on the basis of several replicates. This phenomenon is explained in part by the presence of a measurement background noise, which proves to be all the more predominant in the calculation of the modulation coefficient when the genes are weakly expressed.

The differential analysis according to the "Global Error Assessment" (GEA) method disclosed in the document referenced above makes it possible to correct this bias. It consists in grouping the genes together according to a statistical criterion, called significance (or p-value), taking into account the variability in the modulation coefficient as a function of the level of expression under the reference condition for each gene. The variability in the modulation coefficient is, for a given gene, the standard deviation of the modulation coefficients with a mean modulation coefficient. This p-value reflects the significance of a modulation coefficient value. This makes it possible to obtain groups of genes corresponding to a given p-value and to equilibrate, in the list of selected genes, the proportion of genes weakly expressed under the reference condition.

However, the p-value has no biological meaning. As a result, biologists, who reason in the world of modulations, cannot use this value as a basis for identifying the differentiated genes. Consequently, they cannot use the "GEA" method for finding the differentiated genes.

In practice, after one or more differential analyses, biologists most commonly use classification and visualization techniques in order to identify genes exhibiting expression modulation profiles that are similar from several conditions. This involves, for example, the technique of hierarchical classification or classification by robust singular value decomposition disclosed in the document L. Liu et al., Robust singular value decomposition analysis of microarray data, PNAS, 2003.

However, in these techniques, owing to display-related limitations, or in order to concentrate on more complex analyses such as ontological analyses or analyses relating to metabolic pathways, biologists are prone to limit the size of the lists of selected genes. Thus, they rely on the expression modulation levels measured under each condition, and do not therefore take into account the associated significance. The information relating to this significance is thus lost during the visualization of the modulation levels after classification. In other words, biologists simply consider the ratio of the level of expression of genes from two conditions, classified in decreasing order according to their modulation coefficient. This is standard modulation.

Generally wishing to visualize the genes most highly modulated under the treatment condition, biologists then apply decreasing sorting according to the level of modulation and conserve only the first genes. In doing so, they do not take into account the significance and reintroduce the selection bias that had been removed by the calculation of the p-value.

SUMMARY OF THE INVENTION

Given the above, one problem addressed by the present invention is that of carrying out a corrective method for processing results of transcriptome experiments obtained by differential analysis, which takes into account the significance associated with the modulation coefficient values, and the result of which can, in addition, be exploited using values that have a biological meaning.

The present invention thus features a corrective method for processing results of transcriptome experiments obtained by differential analysis, comprising the following steps:

obtaining the results of the level of expression of genes under a reference condition, and calculating the mean level of expression of each of said genes;

obtaining the results of the level of expression of said genes under a treatment condition, and calculating the mean level of expression for each of said genes;

calculating the modulation coefficient for the level of expression for each of said genes;

calculating a p-value associated with each modulation coefficient; and calculating isobar curves of p-value as a function of the mean level of expression of each of said genes under the reference condition; and which further comprises a step of calculating and associating a median modulation coefficient on the isobar curve of each p-value observed.

Advantageously, said steps of calculating a p-value associated with each modulation coefficient and of calculating a median modulation coefficient according to the isobar curve of each p-value observed are carried out by means of the "GEA" method; said steps of obtaining the results of the level of expression of genes under one (or more) reference condition(s), of obtaining the results of the level of expression of genes under one (or more) treatment condition(s), of calculating the modulation coefficient (variation) for the level of expression, of calculating the p-value, and of calculating a median modulation coefficient on the isobar curve of each p-value observed are carried out for a plurality of different treatment conditions; said step of calculating isobar curves of p-value as a function of the mean level of expression of each of said genes under the reference condition comprises a representation, by a dot, of each gene studied, on a graph displaying, along the x-axis, the logarithm of the mean level of expression under the reference condition denoted x, and, along the y-axis, the logarithm of the mean level of expression under the treatment condition, denoted y, an isobar curve of level p corresponding to the theoretical dots for which the p-value is equal to p; a user selects genes of interest on the basis of a value having a biological meaning; said value having a biological meaning is a modulation coefficient value; a user selects genes of interest on the basis of a value having a significance; the transcriptome experiments are carried out on DNA chips.

The present invention also features a computer for implementing a corrective method for processing results of transcriptome experiments obtained by differential analysis according to the invention.

Figure 1:
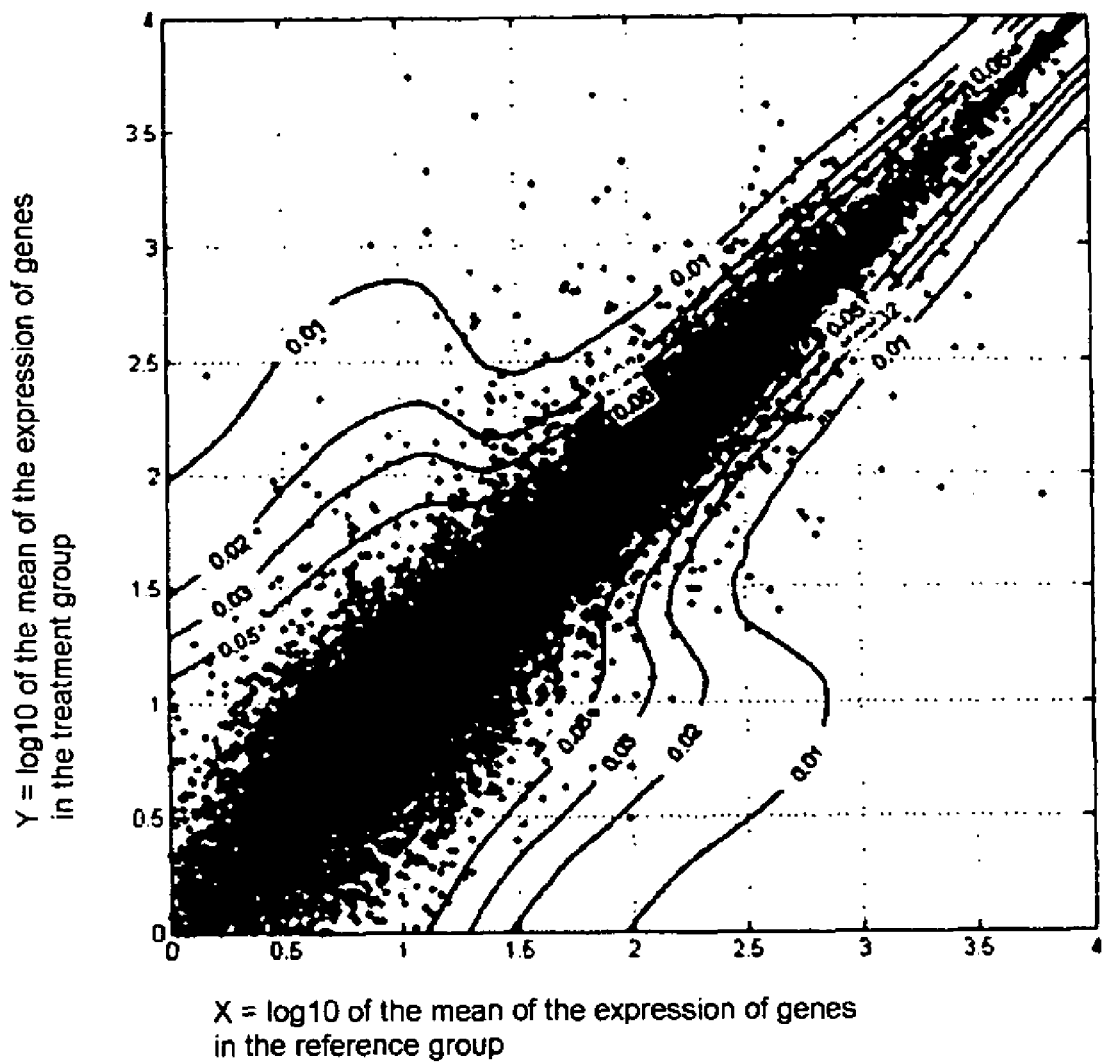
FIG. 1 is, in the form of a graph, the results of transcriptome experiments, and also the isobar curves of p-value, such as they can be obtained according to one embodiment of the present invention.

DETAILED DESCRIPTION OF BEST MODE AND SPECIFIC/PREFERRED EMBODIMENTS OF THE INVENTION

The processing method according to the invention is a corrective method which makes it possible to process results of transcriptome experiments, and in particular to process results of transcriptome experiments carried out on DNA chips.

The transcriptome experiments carried out on DNA chips are able to be performed in the following way.

Cells are cultured under at least two different conditions. The first condition is termed "reference" condition. It serves as a control. The second condition is termed "treatment" condition. Under the treatment condition, the cells are cultured either in the presence of a particular agent, for example a protein or an antibiotic, or under particular experimental conditions, for example luminosity, oxygenation, pH or pressure conditions.

In practice, each culture is advantageously carried out several times for the same condition. A plurality of replicates is then obtained. The term "plurality of replicates" means preferably three or four cultures carried out under a reference condition, and two cultures carried out under the same treatment condition. The results obtained from several replicates enable a statistical analysis to be performed.

Independently for each replicate, the cells are lysed and the nucleic acids of these cells are solubilized. The mRNAs are then purified by passing them over a column containing beads to which oligo-dT oligomers are attached. In fact, the mRNAs, which have a polyadenylated tail, are obtained by the beads of the column, whereas the other nucleic acids are eliminated.

After elution, the mRNAs purified for each replicate are recovered. Fluorescent cDNAs are then synthesized from the mRNAs obtained. To do this, either oligo-dT primer, or primers specific for each mRNA, or random primers, hybridize with the purified mRNAs and an enzyme, reverse transcriptase, makes it possible to synthesize the cDNA strand. The use of fluorescent nucleotides makes it possible to obtain labeled cDNAs. The mRNAs are degraded so as to then conserve only the single strands of fluorescent cDNAs.

The levels of expression of the genes for each replicate are measured by means of a DNA chip. Such a chip conventionally comprises several thousand wells. Several thousand examples of the same coding sequence are attached in each well and this coding sequence is different from one well to the other.

The DNA chip is brought into contact with the solution comprising the fluorescent cDNAs. These cDNAs hybridize specifically on the sequence which is complementary thereto.

After one or more washing steps, the chip is placed in a detection instrument and scanned using a laser which excites the fluorochromes.

For each well, a fluorescence intensity is then determined. This intensity is proportional to the amount of fluorescent cDNA band. Each intensity is proportional to the level of expression of the gene under consideration. Consequently, on the basis of the fluorescence intensities, an expression level value is obtained for each gene analyzed and for each experiment.

The present invention features a corrective method for processing results of transcriptome experiments obtained by differential analysis of the gene expression values, the objective of which is to select the genes most highly modulated, i.e., most strongly overexpressed, and/or most strongly inhibited, under the treatment condition(s) compared to the reference condition.

In particular, the technique according to the present invention comprises a step of calculating the mean level of expression of each gene analyzed, from all the replicates of the same condition. Said method subsequently comprises, for each gene, calculating an expression modulation coefficient, i.e., the ratio from the average level of expression of said gene under the treated condition and under the reference condition.

In another step of the method according to the invention, for each gene analyzed, a p-value is calculated, associated with the modulation coefficient for said gene. This statistical value reflects the chance of observing a difference, at least of a certain level, from the levels of expression of the gene under two different conditions, although, in reality, these levels of expression are identical. In other words, this p-value reflects the degree to which the value of a modulation coefficient is significant, or is, on the contrary, due to a background noise. Thus, this p-value takes into account the variability of the modulation coefficient for the level of expression of said gene. Various methods, such as, for example, the "GEA" method, are applicable to the present method for determining this p-value.

Another step of the processing method according to the invention comprises calculating isobar curves of the p-value as a function of the mean level of expression under the reference condition. This step can be represented by means of a graph, as is shown in FIG. 1. For this, each gene studied is represented by a dot, on a graph displaying, along the x-axis, the logarithm of the mean level of expression under the reference condition, denoted x, and, along the y-axis, the logarithm of the mean level of expression under the treatment condition, denoted y. An isobar curve of level p corresponds to the theoretical points for which the p-value is equal to p. The process for constructing the isobar curves is the following:

1) a sufficiently fine grid of the xy plane defined by the extreme expression values observed is constructed;

2) for each of the dots of the grid, the difference y−x from the treatment condition and the reference condition is determined and is divided by the standard deviation associated with the mean level of expression $(x+y)/2$. For these purposes, the relationship existing from the level of expression and variance of a gene would have been pre-established on the basis of the replicates of the reference condition, in accordance with the GEA method;

3) the isobar curves corresponding to the triplicates (x,y,p-value(x,y)) are plotted by means of a customary method for obtaining contours (for example reference Matlab). For the same p-value, the overexpressed genes are grouped together on one curve, whereas the repressed genes are grouped together on another curve.

The final step of the method entails, for each isobar curve of the p-value, in associating with it the median modulation of the dots contained in this curve. For these purposes, one takes all the dots of the grid along the x-axis, and associates therewith, along the y-axis, the corresponding dots on the isobar curve. Corresponding to each of the dots (x,y) thus obtained is a modulation $\exp(y-x)$. In the calculation of the median per se, each dot (x,y) is weighted by the density of genes observed under the reference condition around the value x.

Since the corrective modulation is by construction a monotonic function of the p-value, it makes it possible to obtain the same gene sortings as the methods according to the prior art, and with, advantageously, levels of corrective modulation that are better distributed. In particular, the sortings do not comprise aberrant values subsequent to expressions reaching, under one of the conditions, a level which is very low, and therefore not very reliable since it is below the threshold of detection of the DNA chips. Thus, the technique according to the invention makes it possible to obtain a better distribution of the genes weakly expressed under the reference condition, among the most highly modulated genes.

Advantageously, the results are analyzed in the domain of modulation levels, and the selections, or list sortings, are carried out in the same domain, and not the domain of p-values. In particular, the method according to the invention takes into account the variability of the modulation coefficients as a function of the level of expression for each gene, of the associated significance and of the median level of modulation, in order to identify profiles of similar modulation, at the same time not losing any significant information.

More advantageously, the method according to the invention allows biologists to reason in one and the same area, to conserve their habits and to overcome the prejudice according to which it is not possible to work by taking into account the p-value or at the same time keeping a biological meaning for the results. In fact, biologists can from now on choose a biological value, and no longer a statistical value, as a threshold for selecting genes of interest. Specifically, they can from now on select the genes of interest that, according to their judgment, are sufficiently modulated, directly on the basis of a modulation coefficient threshold value having a biological meaning and an associated significance. Since the method according to the invention has grouped the genes together in subsets, both as a function of the median value of their modulation coefficient, and as a function of the significance of these modulation coefficients, the biologist then selects genes as a function of the significance of their modulation coefficient.

Figure 2A:
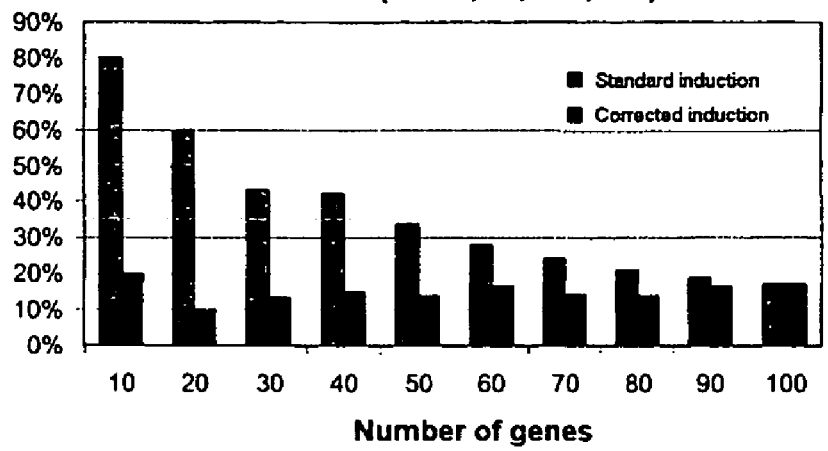
FIGS. 2A and 2B represent, in the form of histograms, the distribution of the weakly expressed genes, i.e., the genes of which the expression is less than 50 (2A) or less than 20 (2B) (arbitrary unit related to the Affymetrix™ technology), among the genes the most highly modulated, resulting from the analysis of transcriptome experiments, firstly, according to the standard modulation method and, secondly, according to the invention, termed corrective modulation method.
Figure 2B:
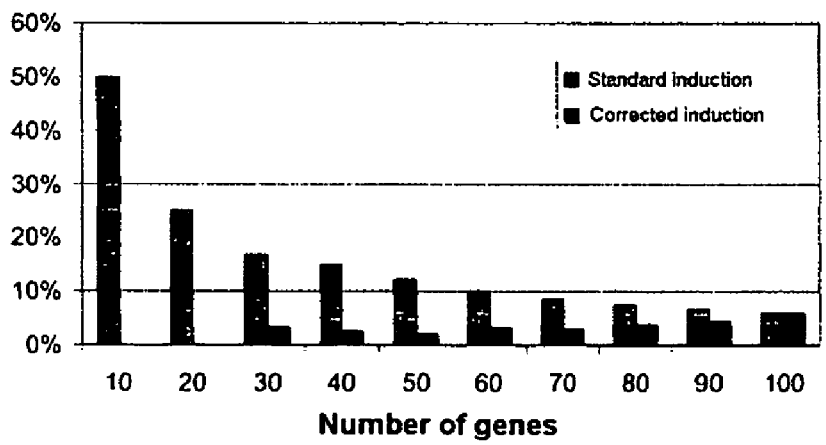

FIGS. 2A and 2B represent differential analyses of results of transcriptome experiments obtained from a treatment condition compared with a reference condition (culture of rat preputial sebocytes in the presence (treatment condition) or absence (reference condition) of a PPARgamma agonist, the CD4700 compound).

In FIG. 2A, the genes most strongly modulated are selected and the percentages of genes having an expression intensity of less than 50 (arbitrary unit related to the Affymetrix™ technology), among the first genes selected, are represented in the form of histograms. These selections are carried out, on the one hand, with the corrective modulation method according to the invention and, on the other hand, with the standard method of the prior art. When comparing these two methods, it is noted that the method according to the invention standardizes the distribution of these weakly expressed genes. In other words, by applying the corrective modulation method according to the invention, one obtains approximately 15% of genes having an expression intensity of less than 50, when the 10 most highly modulated genes or the 100 most highly modulated genes are selected. Conversely, the abovementioned method of the prior art does not give uniform results. For example, with the standard method, among the 10 most highly modulated genes, one finds 80% of genes having an expression intensity of less than 50.

In FIG. 2B, the genes most strongly modulated are selected and the percentages of genes having an expression intensity of less than 20 (arbitrary unit related to the Affymetrix™ technology), among the first genes selected, are represented in the form of histograms, according to the corrective modulation method and according to the standard modulation method. In a manner similar to FIG. 2A, a standardization of the distribution of genes having an expression intensity of less than 20 is obtained among the most highly modulated genes selected with the corrective modulation method according to the invention.

In another example, which is not represented, a differential statistical analysis of gene expression was carried out by means of a DNA chip, the reference of which is RAE230A, these genes being modulated by a PPARgamma agonist. Two methodologies were followed in order to study the genes, corresponding to the Affymetrix™ identifiers contained in the wells of the chip, as a function of the level of expression of the genes: the "standard" methodology, corresponding to the "GEA" method, and the "corrective" methodology of the invention. The two lists obtained were sorted as a function of the level of expression of the genes, by decreasing order. The first 50 Affymetrix™ identifiers of each list were analyzed with the GOTM™ web application described in the following publication, Zhang B, Schmoyer D, Kirov S, Snoddy J. (2004), BMC Bioinformatics, 18; 5(1): 16.

If one considers an ontology relating to "lipid metabolism", which constitutes one of the ontologies most significantly affected from a statistical point of view, it appears that, with the standard method, 7 Affymetrix™ identifiers corresponding to 5 genes are extracted, whereas, with the method according to the invention, 10 Affymetrix™ identifiers corresponding to 7 genes were identified.

It is clearly understood that the corrective according to the invention can, in practice, be implemented by a personal computer equipped at least with a microprocessor and associated ROM and RAM memories. It then constitutes an item of software, the execution of which is controlled by a biologist or another operator, in order to obtain corrective results of transcriptome experiments. This software can, moreover, be saved on any memory media possibly of the non-volatile type, such as CD-ROMs or diskettes.

Each patent, patent application, publication, text and literature article/report cited or indicated herein is hereby expressly incorporated by reference in its entirety.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A corrective method for processing results of transcriptome experiments obtained by differential analysis, comprising the following steps:
    obtaining the results of a level of expression of genes under a reference condition, and calculating a mean level of expression of each of said genes;
    obtaining the results of the level of expression of said genes under a treatment condition, and calculating the mean level of expression for each of said genes;
    calculating a modulation coefficient for the level of expression for each of said genes;
    calculating a p-value associated with each modulation coefficient;
    calculating isobar curves of p-value as a function of the mean level of expression of each of said genes under the reference condition;
    calculating and associating a median modulation coefficient on the isobar curve of each p-value observed; and
    selecting genes exhibiting a predetermined modulation coefficient.

2. The method as defined by claim 1, wherein said steps of calculating the p-value associated with each modulation coefficient and of calculating the median modulation coefficient according to the isobar curve of each p-value observed are carried out by a global error assessment ("GEA") method.

3. The method as defined by claim 1, wherein said steps of obtaining the results of the level of expression of genes under the reference condition, of obtaining the results of the level of expression of genes under the treatment condition, of calculating the modulation coefficient for the level of expression, of calculating the p-value, and of calculating the median modulation coefficient on the isobar curve of each p-value observed, are carried out for a plurality of different treatment conditions.

4. The method as defined by claim 1, wherein said step of calculating isobar curves of p-value as the function of the mean level of expression of each of said genes under the reference condition comprises a representation, by a dot, of each gene studied, on a graph representing, along an x-axis, logarithm of the mean level of expression under the reference condition, denoted x, and, along a y-axis, logarithm of the mean level of expression under the treatment condition, denoted y, the isobar curve of level p corresponding to the theoretical dots for which the p-value is equal to p.

5. The method as defined by claim 1, wherein a user selects genes of interest on a basis of a value having a biological meaning.

6. The method as defined by claim 5, wherein said value having the biological meaning is the modulation coefficient value.

7. The method as defined by claim 1, wherein a user selects genes of interest on a basis of a value having a significance.

8. The method as defined by claim 1, wherein the transcriptome experiments are carried out on DNA chips.

9. A non-transitory computer readable medium encoded with a program to be installed in a device with a microprocessor, wherein said device comprises a storage section stored with processing information, and wherein said program causes said microprocessor to execute a corrective method for processing results of transcriptome experiments obtained by differential analysis, the method comprising the following steps:
    obtaining the results of a level of expression of genes under a reference condition, and calculating a mean level of expression of each of said genes;
    obtaining the results of the level of expression of said genes under a treatment condition, and calculating the mean level of expression for each of said genes;
    calculating a modulation coefficient for the level of expression for each of said genes;
    calculating a p-value associated with each modulation coefficient;
    calculating isobar curves of p-value as a function of the mean level of expression of each of said genes under the reference condition; and
    calculating and associating a median modulation coefficient on the isobar curve of each p-value observed.

* * * * *